(12) United States Patent
Gardner

(10) Patent No.: US 8,556,863 B2
(45) Date of Patent: Oct. 15, 2013

(54) NEEDLE SHEATH REMOVAL APPARATUS

(75) Inventor: Richurd Gardner, Boscawen, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 866 days.

(21) Appl. No.: 12/230,132

(22) Filed: Aug. 25, 2008

(65) Prior Publication Data

US 2010/0049141 A1 Feb. 25, 2010

(51) Int. Cl.
*A61M 5/32* (2006.01)

(52) U.S. Cl.
USPC ............ 604/198; 604/192; 604/210

(58) Field of Classification Search
USPC .......... 604/192, 198, 263, 197, 110, 246
See application file for complete search history.

(56) References Cited

U.S. PATENT DOCUMENTS

| | | | | |
|---|---|---|---|---|
| 4,982,842 A | * | 1/1991 | Hollister | 206/365 |
| 5,512,049 A | * | 4/1996 | Fallas | 604/192 |
| 2002/0091360 A1 | * | 7/2002 | Peters, III | 604/198 |
| 2005/0148941 A1 | * | 7/2005 | Farrar et al. | 604/189 |

FOREIGN PATENT DOCUMENTS

JP 06121836 A * 5/1994

OTHER PUBLICATIONS

Machine translation of JP 06-121836.*

* cited by examiner

*Primary Examiner* — Kevin C Sirmons
*Assistant Examiner* — Brandy S Lee
(74) *Attorney, Agent, or Firm* — Louis Woo

(57) ABSTRACT

A needle protective housing used to cover a contaminated needle after use is configured to have at least one cam positioned below the lip of the sheath attached to the base of the needle device for covering the needle prior to use. When the sheath is attached to the base of the needle device, the needle protective housing is positioned in proximity to the sheath. To remove the sheath, a user would pivotally move the needle protective housing in a direction away from the sheath so that the cam coacts against the lip of the sheath in an upward direction as the needle protective housing is pivoted downwards relative to the needle device. The cam may be an integral extension of the needle protective housing, or it may be a clip retrofittable to the needle protective housing.

17 Claims, 7 Drawing Sheets

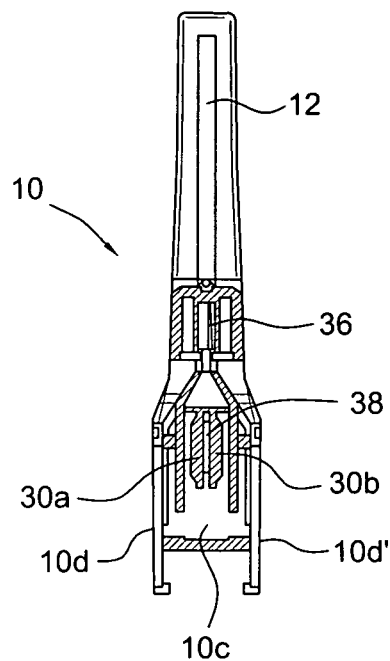
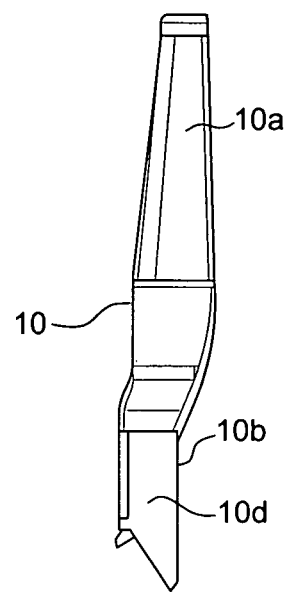
FIG. 5A
FIG. 5B
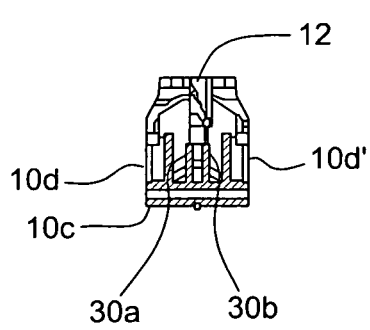
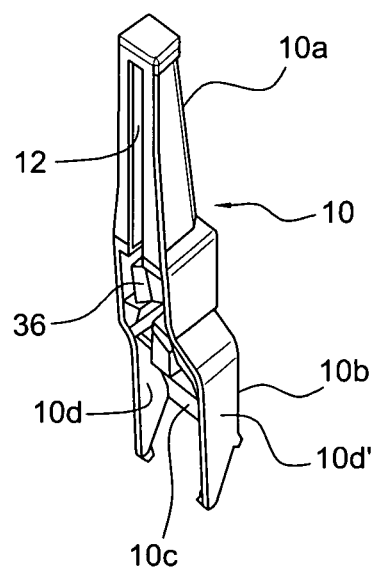
FIG. 5C
FIG. 5D

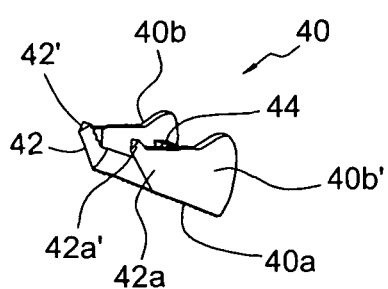 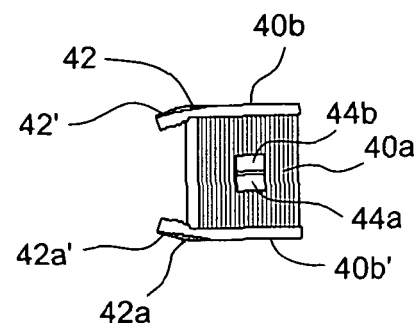
FIG. 6A  FIG. 6B
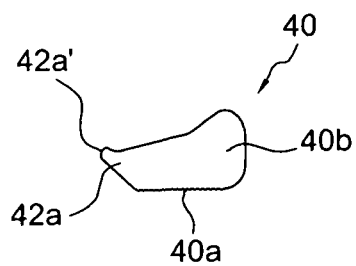 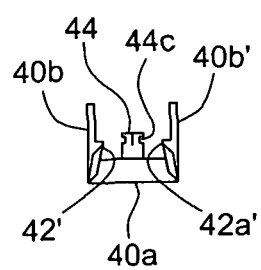 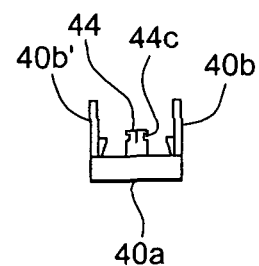
FIG. 6C  FIG. 6D  FIG. 6E

NEEDLE SHEATH REMOVAL APPARATUS

FIELD OF THE INVENTION

The present invention relates to needle devices such as syringes that have a needle assembly attached thereto or fixed needle syringes, and more particularly to a sheath removal mechanism that enables a user to remove the sheath that covers the needle of such a needle device prior to its use without using both hands.

BACKGROUND OF THE INVENTION

Sheathed needle devices are not new. Some sheathed needle devices include a needle protective housing pivotally hinged to the base of the needle. Once the sheath that covers the needle prior to its use has been removed and the needle presumably having been used, the needle protective housing is moved to cover the needle to prevent the contaminated needle from being further exposed. Among patents disclosing needle devices that have a needle protective housing hingedly connected to the base of the needle, the following are assigned to the same assignee of the instant application: U.S. Pat. No. 5,139,489, U.S. Pat. No. 5,277,311, U.S. Pat. No. 5,154,285, U.S. Pat. No. 5,232,455, U.S. Pat. No. 5,277,311, U.S. RE37, 110 and U.S. RE37,252. For these devices, as shown for example in U.S. RE37,252, prior to use, the needle is covered by a sheath. To use, the needle device is held with one hand, while the sheath is removed by the other hand. After use, the needle protective housing is pivoted in a direction toward the needle to cover the contaminated needle.

That a sheathed needle device requires a two-handed operation means that the clinician has to have both hands free, one hand holding the needle device while the other hand being used to remove the sheath. But oftentimes while the clinician is holding the sheathed needle device with one hand, her other hand is holding something else that requires that she continues to hold. There is therefore a need for a sheathed needle device that is designed to have its sheath removed by a one handed operation, in that the hand of the clinician that is holding the sheathed needle device is also adaptable to remove the sheath from the needle device.

BRIEF DESCRIPTION OF THE PRESENT INVENTION

The needle device of the instant invention is configured to have at the proximal end of the needle protective housing at least one cam that is positioned below the lip at the open end of the sheath that covers the needle that extends from the base prior to use. The sheath is frictionally mated to and in contact with the base of the needle device such that it is not removable from the base without a user having to apply a predetermined force longitudinally along the axis of the base to pull the sheath off the base. Utilizing the pivotal movement of the needle protective housing, the cam is configured such that it extends from the proximal end of the needle protective housing to be positioned below the open end of the sheath when the needle protective housing is located at a first position at a small angle proximate to the longitudinal axis of the base of the needle device, with the sheath covering the needle and its open end mated to the base of the needle device.

To remove the sheath from the base of the needle device, a user would use one of her digits, possibly her thumb, to move the needle protective housing in a direction away from the longitudinal axis of the base, while holding the needle device—be it a needle assembly mated to a syringe, a fixed needle syringe or another type of needle device for example a Vacutainer holder. Such pivotal movement of the needle protective housing applies the required predetermined force longitudinally along the axis of the base upwardly against the sheath. As a result, as the needle protective housing is moving away from the longitudinal axis of the needle device, the sheath that covers the needle is automatically removed. The user can thereafter readily use the needle since the needle protective housing is now at a second position at a greater angle away from the needle and the longitudinal axis of the base and therefore does not interfere with the use of the needle.

The cam that extends from the proximal end of the needle protective housing proximate to the base of the needle device may extend from the back wall of the housing. Alternatively, two cams may be provided at the proximal end of the housing, with each cam extending from a corresponding sidewall of the housing so that the respective tips or fingers of the cams are at opposite sides of the base to apply even pressure to the sheath to remove it from the base, when the needle protective housing is pivotally moved away from the base.

The cam(s) may be formed as an integral extension from the needle protective housing. The needle protective housing likewise is formed as an integral extension of the needle base. Thus, the cam, the needle protective housing and the base are all molded as a one-piece unit or component. Alternatively, the cam may be a separate molded clip piece retrofitted to the needle protective housing, for example at a lower portion at the back wall of the housing. For such retrofitting, respective retainer mechanisms are provided or integrated to the housing and the cam. The respective retainer mechanisms at the housing and the cam clip may be corresponding aperture/anchor formed at those components.

The instant invention is therefore directed to an apparatus that comprises a base with a needle end to which a needle extends, a needle protective housing pivotably connected to the base, a sheath non-fixedly mated to the base to cover the needle extending therefrom prior to the use thereof, the sheath having an open end that frictionally contacts the base so as not to be removable from the base without a predetermined force applied thereto longitudinally along the axis of the base or the needle in order to remove it from the base, the sheath having a circumferential lip at its open end, wherein the housing comprises finger means that are positioned below the lip of the sheath with the housing being in a first position in relative proximity to the sheath when the sheath is mated to the base and covers the needle, the finger means applying at least the predetermined force against the lip of the sheath to remove the sheath from the base when the housing is pivotally moved from the first position in a direction away from the longitudinal axis of the base or the needle toward a second position.

Another aspect of the instant invention is directed to a needle assembly that comprises a base with a needle end to which a needle extends and a receptacle end adapted to connect the needle assembly to a luer of a syringe, a needle protective housing pivotably connected to the base, a sheath non-fixedly mated to the base to cover the needle extending therefrom prior to the use thereof, the sheath having an open end that frictionally contacts the base so as not to be removable from the base without a predetermined force applied thereto longitudinally along the axis of the base toward the needle to remove it from the base, wherein the housing comprises at least one cam positioned adjacent to the opening of the sheath with the housing being in a first position in relative proximity to the sheath when the sheath is mated to the base and covers the needle, the cam applying at least the predetermined force against the sheath to remove the sheath from the base when the housing is pivotally moved from the first position toward a second position away from the longitudinal axis of the base.

Yet another aspect of the instant invention is directed to a device for removing a sheath from the needle assembly having a base to which the sheath is removably mated, the sheath covering a needle extending from the base, the sheath having an open end that frictionally contacts the base so as not to be removable from the base without a predetermined force applied thereto longitudinally along the axis of the base toward the needle, the sheath having a circumferential lip at its open end, the device comprising a needle protective housing pivotably connected to the base having at least one cam positioned below the lip of the sheath with the housing being at a first position in relative proximity to the sheath when the sheath is mated to the base and covers the needle, the cam applying at least the predetermined force against the sheath to remove the sheath from the base when the housing is pivotally moved from the first position toward a second position away from the longitudinal axis of the base.

BRIEF DESCRIPTION OF THE FIGURES

The present invention will become more apparent and the invention itself will be best understood by reference to the following description of an embodiment of the invention taken in conjunction with the following drawings, wherein:

FIG. 5a is a plan view of a needle protective housing;

FIG. 5b is a side view of the needle protective housing of FIG. 5a;

FIG. 5c is an end view from the proximal end of the FIG. 5a housing;

FIG. 5d is a perspective view of the FIG. 5a housing;

FIG. 6a is a perspective view of a cam mechanism in the form of a clip combinable with the needle protective housing of FIGS. 5a-5d;

FIG. 6b is a plan view looking into the interior of the FIG. 6a cam mechanism;

FIG. 6c is a side view of the FIG. 6a cam mechanism;

FIG. 6d is an end view of the FIG. 6a cam mechanism showing the fingers of the cam mechanism;

FIG. 6e is another end view of the FIG. 6a cam mechanism;

DETAILED DESCRIPTION OF THE INVENTION

Figure 1A:
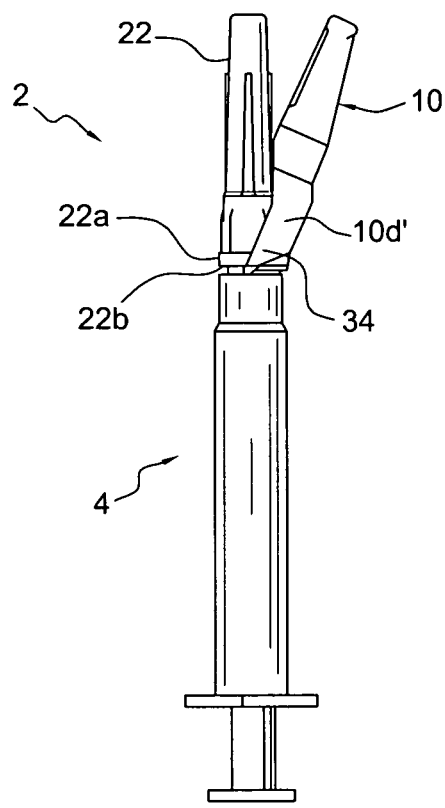
FIG. 1a is a side view of a syringe fitted with a needle assembly of the instant invention.

With reference to FIGS. 1a-1b and FIGS. 2a-2b, a first embodiment of a needle device that has the one-handed sheath removal apparatus is shown. In particular, a needle mechanism in the form of a needle assembly 2 coupled to a syringe 4 is shown to have a needle base 6 to which a needle or cannula 8 extends from a needle hub 6a that is at a distal or patient end of base 6. Base 6 further includes a proximal end 6b that has a luer that allows needle assembly 2 to be matingly coupled to a counterpart luer end of a syringe, such as 4 shown in FIGS. 1a and 1b.

Figure 2A:
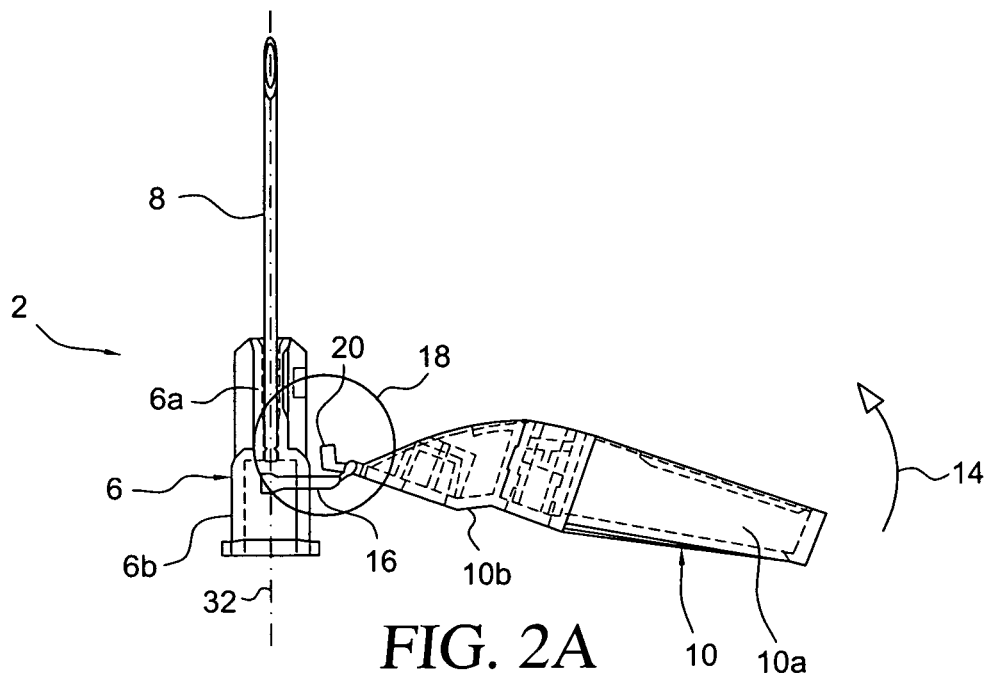
FIG. 2a is a side view of a needle assembly of the instant invention.
Figure 2B:
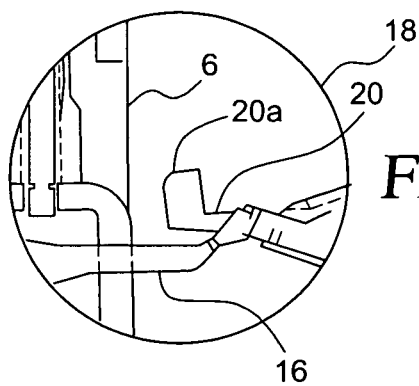
FIG. 2b is an enlarged view of the circled portion of the FIG. 2a needle assembly.
Figure 2C:
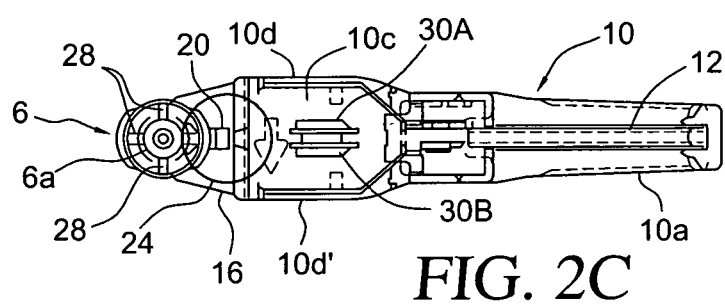
FIG. 2c is a plan view showing the interior of the housing of the FIG. 2a needle assembly and the connection of the housing with the cam mechanism to the needle base.
Figure 2D:
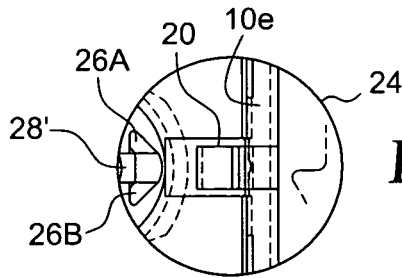
FIG. 2d is an enlarged view of the circled portion of the needle assembly shown in FIG. 2c.
Figure 3C:
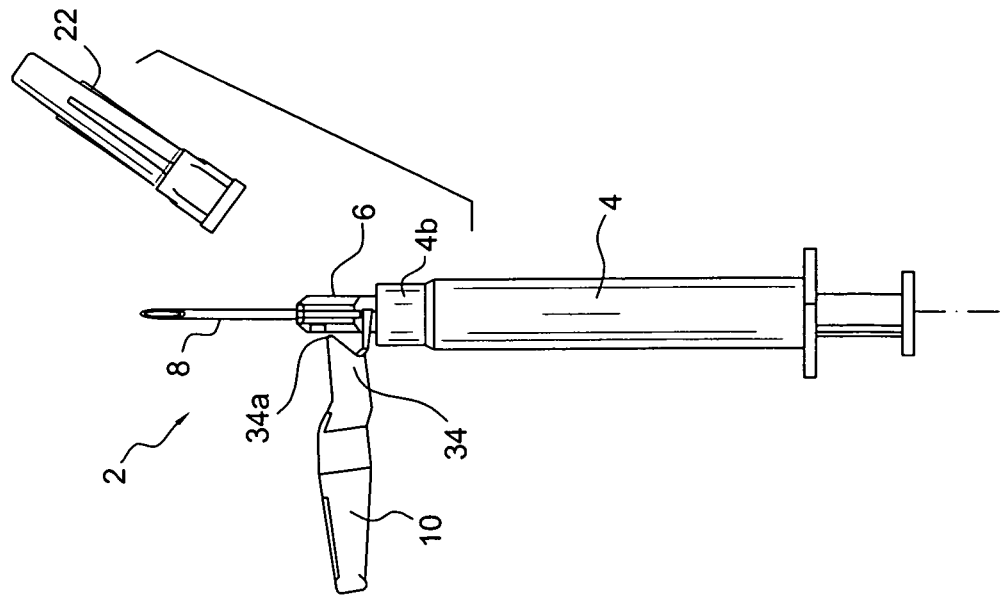
FIGS. 3a-3c show a syringe fitted with the sheath removal apparatus of the instant invention and in particular show the movement of the needle protective housing traveling from a position proximate to the sheath to a position away from the sheath, and the corresponding movements of the sheath during its removal.
Figure 3B:
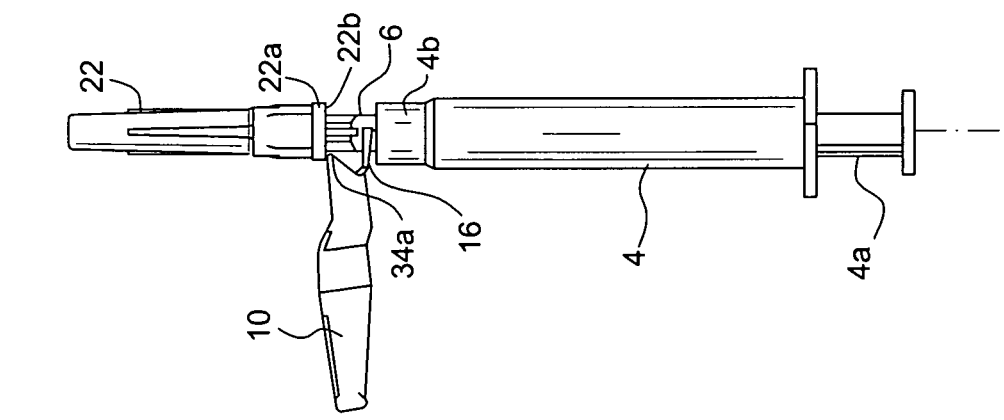

Needle assembly 2 for the instant invention is further shown to include a needle protective housing 10 that has a main portion 10a that, as best shown in FIG. 3b, has a slot 12 that allows needle 8 to pass into housing 10, when housing 10 is pivoted in the direction as indicated by directional arrow 14. Housing 10 also has a lower portion 10b that is pivotally connected to base 6, by way of a living hinge 16. As best shown in the enlarged illustration of the circled portion 18 of FIG. 2b, there is a finger means in the shape of a cam 20 having a finger portion 20a that extends from the lower edge of the lower portion 10b of housing 10. In FIG. 2b, finger 20a is shown to be pointed upwards toward the tip of needle 8. For the needle assembly 2 shown in FIGS. 2a-2d, a needle sheath that is mated to base 6 for covering needle 8 prior to needle 8 being used is not shown. Such sheath is shown in FIGS. 1a and 1b with designation 22.

With reference to FIG. 2c, housing 10 is shown to have a back wall 10c and two sidewalls 10d and 10d' that together form an enclosed portion 10c, with a slot 12 formed thereat to allow needle 8 to pass into housing 10, when housing 10 is pivoted in the direction as indicated by directional arrow 14. As further shown, cam 20 extends from the lower edge of the lower portion 10b of housing 10 so as to be substantially in the middle of housing 10. The lower edge of housing 10 is designated 10e in the enlarged circled illustration 24, per shown in FIG. 2d. The illustration in FIG. 2d further shows two hooks 26a and 26b that extend from a rib 28 that extends from the patient end 6a of base 6. As best shown in FIG. 2c, there are four ribs 28 extending from the patient end 6a of the needle hub. As shown in FIG. 2d, one of the ribs 28' faces housing 10. In practice and for the discussion of this invention, ribs 28 may be referred to as a part of the needle hub, or the patient end or the needle end of base 6.

Two loops 30a and 30b that extend from back wall 10c of housing 10 are shown in FIG. 2c. Housing 30a and 30b come into contact with and lockingly mate to hooks 26a and 26b, respectively, when housing 10 is pivotally moved along the direction indicated by directional arrow 14, after needle 8 has passed into the interior of housing 10 and housing 10 substantially is in alignment along the longitudinal axis 32 that runs through needle 8 and base 6.

Figure 1B:
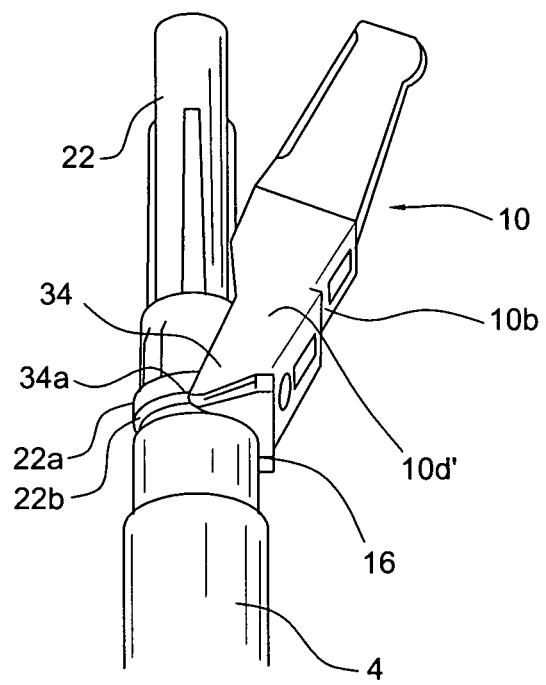
FIG. 1b is an enlarged perspective view of the needle assembly of the instant invention, as attached to the luer end of a syringe.

FIGS. 1a and 1b show the attachment of needle assembly 2 to a syringe 4. The needle assembly 2 shown in FIGS. 1a and 1b is an alternative embodiment of the needle assembly 2 shown in FIGS. 2a-2d. For the further discussion of the instant invention, elements that are the same or have the same functionality for the different disclosed embodiments are labeled the same.

Figure 3A:
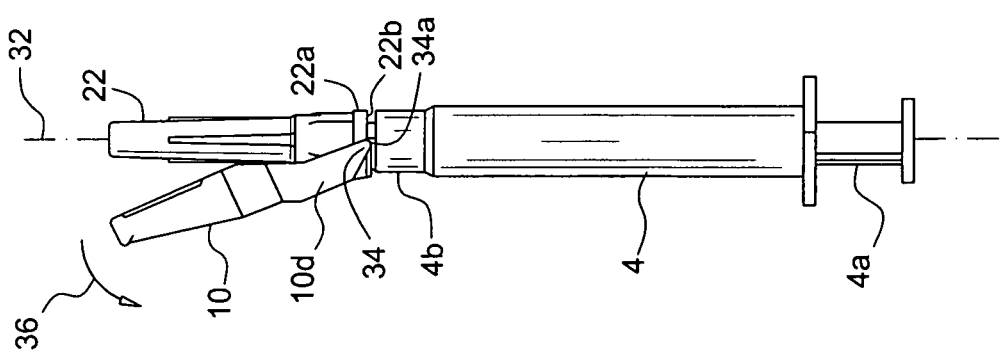

The needle assembly 2 shown in FIGS. 1a and 1b, and illustrated in FIGS. 3a-3c, is different from the needle assembly 2 shown in FIGS. 2a-2d in that the cam mechanism for the FIGS. 1a-1b embodiment comprises two finger means each extending from a corresponding one of the sidewalls of needle protective housing 10. As particularly shown in FIGS. 1a and 1b, at sidewall 10d' of housing 10 there is extended a cam 34 that has a tip or finger 34a that is positioned below the lip 22a at the opening or open end of sheath 22. As shown, lip 22a has a surface 22b that is above or adjacent to finger 34a of cam 34. In other words, finger 34a of cam 34 is below lip 22a of sheath 22. In practice, finger 34a may be adjacent to or be in contact with surface 22b of lip 22a of the sheath 22. In the position shown in FIGS. 1a and 1b, housing 10 is at an angle in relative proximity to the sheath 22, which is covering needle 8 and is frictionally coupled to base 6 of the needle assembly 2.

FIGS. 3a-3c illustrate the removal of sheath 22 from needle assembly 2. Such removal is done in a one-handed fashion by a user, with the user holding the body of syringe 4 with the palm of her hand and a number of her fingers, and moving needle protective housing 10 with one of her digits, for example her thumb per the direction indicated by directional arrow 36. As housing 10 is moved from where it is in close proximity to sheath 22 towards another position substantially at right angle from longitudinal axis 32, cam fingers 34a that extend from each of the sidewalls 10d and 10d' at the lower portion of housing 10 would first come into contact with surface 22d of lip 22a (if they are not already in contact with surface 22d), and then push against lip 22a and therefore sheath 22 with an upwards force. As long as the movement of housing 10 in the direction of directional arrow 36 produces a force via the cams against sheath 22 that exceeds the predetermined force that holds sheath 22 in frictional contact connection to base 6 of the needle assembly, sheath 22 is disengaged from base 6. With housing 10 at the position shown in FIG. 3b, the open end of sheath 22 is no longer in frictional engagement with base 6. Sheath 22 can then readily be removed, as for example by the user turning syringe 4 upside down or sideways so that the sheath can slide off or fall off from the needle assembly. The ejection removal of sheath 22 from needle assembly 2 is shown in FIG. 3c, whereby the removal force by the cams is such that housing 10 may actually be popped off from base 6.

As illustrated in FIGS. 3b and 3c, sheath 22 is disengaged from base 6, and housing 10 has been moved to a second position that is substantially orthogonal to the longitudinal axis 32. But it should be appreciated that the location of the position of housing 10 when sheath 22 is disengaged from base 6 is dependent to a large extent on the design of cam 34, as finger 34a of cam 34 may well be designed to angle in such a way relative to the lip of sheath 22 that housing 10 may only need to be moved to a second position that is 45°, or some other degree less than 90°, from the longitudinal axis 32 in order to force sheath 22 to be disengaged from base 6.

Figure 4A:
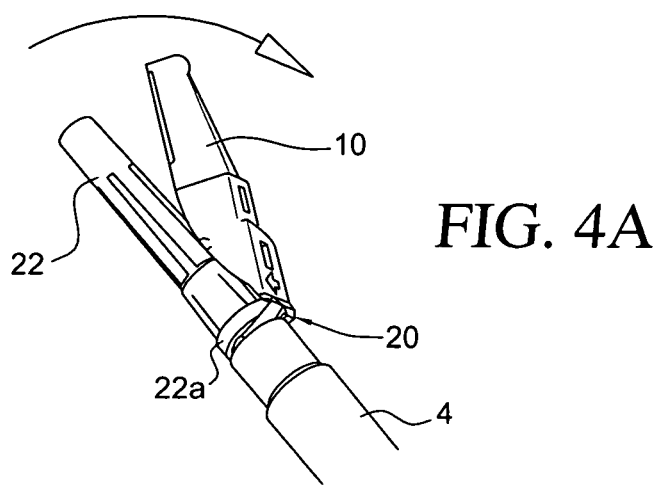
FIGS. 4a-4c illustrate the removal of a sheath from the needle hub by a cam mechanism extending from the back wall of the needle protective housing.
Figure 4B:
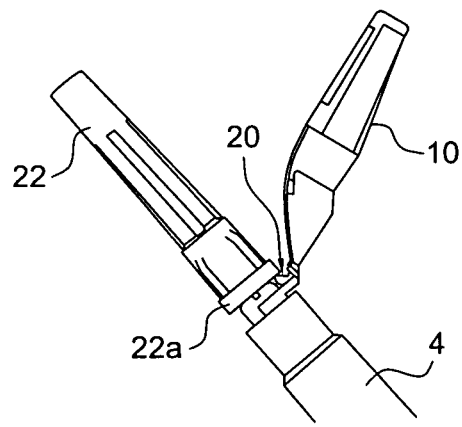
Figure 4C:
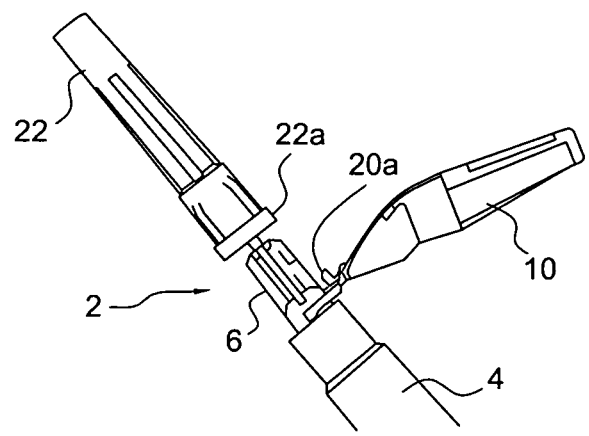

FIGS. 4a-4c are illustrations of the removal of sheath 22 from base 6 of the needle assembly 2 by the use of the cam mechanism shown in FIGS. 2a-2d. In particular, the single cam 20 that extends from the bottom edge of housing 10 is positioned below lip 22a of sheath 22, when housing 10 is in a close proximity position relative to sheath 22, per shown in FIG. 4a. With the user holding syringe 4 and probably plunger 4a with possibly her index, middle and ring fingers, the user can use her thumb to move housing 10 to the second position shown in FIGS. 3b and 3c to forcedly disengage sheath 22 from base 6 of the needle assembly.

Although the needle assembly 2 and syringe 4 shown in FIGS. 1a-1b, 3a-3c and 4a-4d are separate components, it should be appreciated that the cam mechanism provided at housing 10 may be incorporated into a fixed needle syringe where needle 8 extends from the needle hub that is part of a syringe. In other words, the fixed needle syringe is a one-piece syringe that includes the needle hub and the syringe body into which the plunger is inserted, with the needle of the syringe mounted to the needle hub to be in fluid communication with the interior of the barrel of the syringe. For the fixed needle syringe embodiment, there is no luer end 4b that is present in a conventional syringe, per shown by the illustrated syringe 4 in FIGS. 3a-3c. However, the needle of a fixed needle syringe continues to be covered by a sheath, and the needle protective housing with the cam mechanism of the instant invention may be either mounted about the needle hub or the distal end of the syringe, or be molded together with the syringe to effect a one piece unitary fixed needle syringe with the cam fingered needle protective housing of the instant invention.

The cam mechanism is an integral extension of housing 10 in that housing 10 and base 6 are molded as a one piece unit from a single mold. Color pigments may be added to the plastics molding material so that the one piece needle assembly may be molded to have a color that corresponds to the gauge of the needle extending from the needle end of the needle assembly. Thus, be the cam mechanism the unitary finger that extends from the back wall of the housing per shown in FIGS. 2a-2d or the opposing cams that extend from each sidewall of the housing per shown in FIGS. 1a-1b and 3a-3c, the cam mechanism disclosed thus far is an integral extension of the needle protective housing 10.

Instead of being an integral extension of housing 10, the cam mechanism may be a separate component that is retrofitted to housing 10 of a needle device to allow one handed removal of the sheath that covers the needle at the needle device prior to its use.

For ease of illustration, housing 10 is shown by itself in FIGS. 5a-5d. As shown, needle protective housing 10 has an upper closed end portion 10a and a lower portion 10b that has sidewalls 10d and 10d'. As best shown in FIG. 5a, a slot 12 allows the needle to pass through is provided at upper portion 10a and two loops 30a and 30b that engage the anchors 26a and 26b (FIG. 2d) to fixedly hold housing 10 to base 6 are provided at lower portion 10d. For a more securement of needle 8, a hook 36 may also be formed inside housing 10 for grasping needle 8, when the housing is pivotally moved to cover needle 8. There is an aperture 38 (FIG. 5a) at the lower portion of back wall 10c of housing 10.

FIGS. 6a-6e show an add-on cam, in the form of a clip attachable to housing 10, for effecting the cam mechanism of the instant invention. In particular, clip 40 has a back wall 40a and two sidewalls 40b and 40b'. The sidewalls 40b and 40b', as well as back wall 40a, are configured to enable clip to conform to the back and sidewalls at the lower portion 10b of housing 10. At each of sidewalls 40b and 40b' there is a cam portion 42 and 42a, respectively. Cams 42 and 42a have respective fingers 42' and 42a'. There is moreover extending from back wall 40a an anchor 44 that may be made of two pieces 44a and 44b (FIG. 6b) that have an enlarged upper portion with a reduced portion 44c (FIGS. 6d and 6e) configured to fit into aperture 38 (FIG. 5a) of housing 10 so as to securely couple clip 40 to the lower portion of housing 10 when clip 40 is press-fitted to housing 10.

Figure 7:
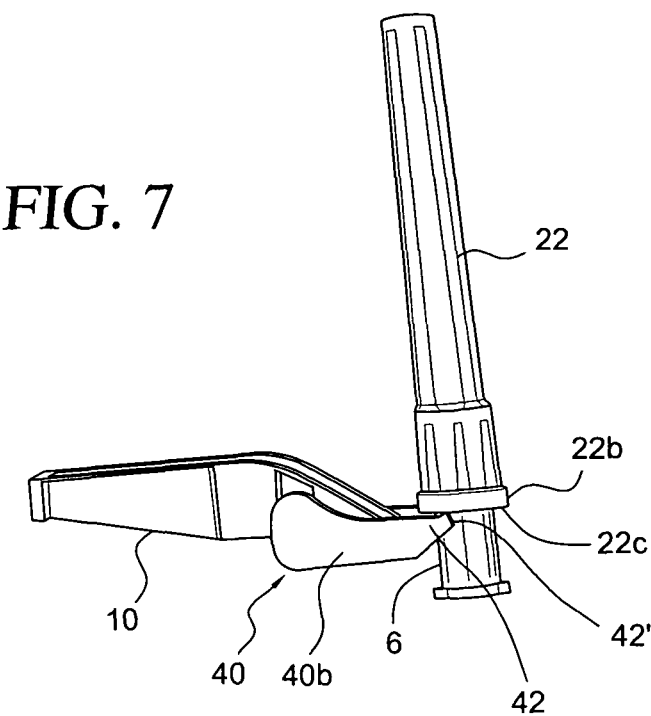
FIG. 7 is a side view illustration of an exemplar needle assembly of the instant invention in which the needle protective housing of FIGS. 5a-5d is fitted with the cam mechanism of FIGS. 6a-6e, with the needle protection housing shown at a position where the sheath is being removed from the needle hub.
Figure 8:
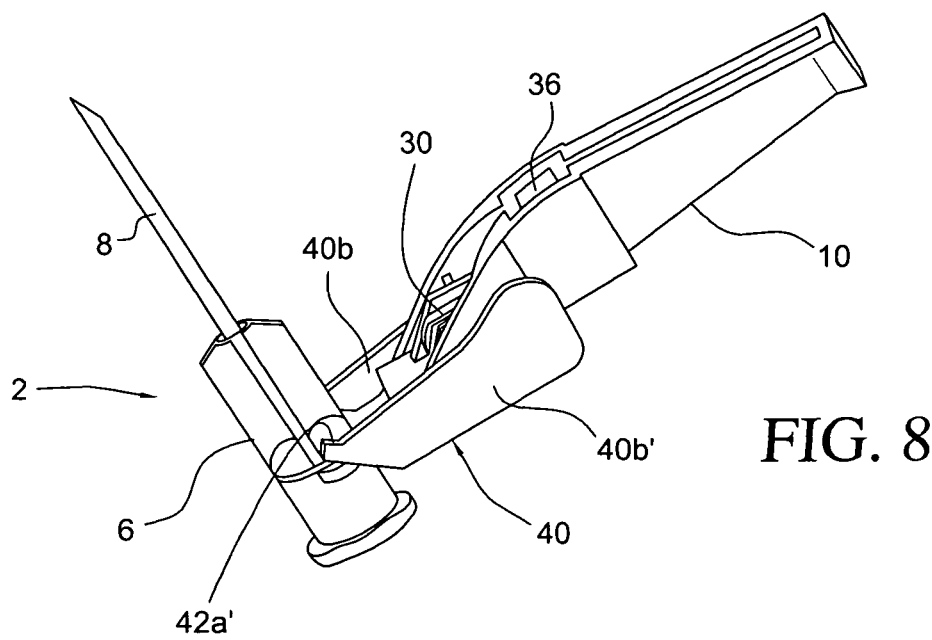
FIG. 8 is a perspective view of the device of FIG. 7 sans the sheath shown in FIG. 7.

FIGS. 7 and 8 each illustrate housing 10 having fixedly coupled thereto clip 40. As shown in FIG. 7, sheath 22 has been substantially disengaged from base 6 by finger 42' of cam 42 (and the not shown opposed finger 42a' of cam 42a) so that sheath 22 is freely resting on base 6 and also cams 42 and 42a. FIG. 8 shows a perspective view of the needle assembly of FIG. 7 with the sheath having been removed.

Even though different embodiments of the inventive needle assembly have been shown in FIGS. 2a and 2d and FIGS. 7 and 8, it should be appreciated that the one handed automatic sheath removal mechanism of the instant invention may also be adapted to be used in other needle devices such as a vacuum tube holder that is disclosed in the above-mentioned U.S. Pat. Nos. 5,139,489 and 5,277,311. The disclosures of the '489 and '311 patents are incorporated by reference herein.

The invention claimed is:

1. Apparatus comprising: a base with a needle end to which a needle extends, a needle protective housing having a back wall and two side walls each extending from the back wall pivotably connected to said base, a sheath non-fixedly mated to said base to cover the needle extending therefrom prior to use thereof, said sheath having an open end that frictionally contacts said base so as not to be removable from said base without a predetermined force applied thereto longitudinally along the axis of said base or needle to remove it from said base, said sheath having a circumferential lip at its open end, wherein said housing comprises finger means that are positioned below the lip of said sheath with said housing being in a first position in relative proximity to said sheath when said sheath is mated to said base and covers the needle, wherein said finger means comprises two cams each extending from a corresponding one of the side walls of said housing, each of said cams having a finger positioned below the lip of said sheath when said housing is at said first position, the finger of each of said cams pushing against the lip of said sheath to remove said sheath from said base when said housing is pivotally moved from said first position in a direction away from the longitudinal axis of said base or needle toward a second position.

2. Apparatus comprising: a base with a needle end to which a needle extends, a needle protective housing pivotably connected to said base, a sheath non-fixedly mated to said base to cover the needle extending therefrom prior to use thereof, said sheath having an open end that frictionally contacts said base so as not to be removable from said base without a predetermined force applied thereto longitudinally along the axis of said base or needle to remove it from said base, said sheath having a circumferential lip at its open end, wherein said housing comprises a back wall and two side walls extending from said back wall, wherein said housing comprises finger means that are positioned below the lip of said sheath with said housing being in a first position in relative proximity to said sheath when said sheath is mated to said base and covers the needle, said finger means applying at least the predetermined force against the lip of said sheath to remove said sheath from said base when said housing is pivotally moved from said first position in a direction away from the longitudinal axis of said base or needle toward a second position, and wherein said finger means comprises a clip separate from said housing but configured to conform with at least the lower portion of said housing so that said clip is attachable to said housing, said clip having at least one cam having a finger positioned below the lip of said sheath when said clip is attached to said housing for pushing against the lip of said sheath to remove said sheath from said base when said housing is pivotally moved toward said second position.

3. Apparatus of claim 2, wherein said back wall comprises an aperture, and wherein said clip comprises an anchor that snap fits into the aperture to fixedly couple said clip to said housing.

4. Apparatus of claim 2, wherein said back wall comprises a first retaining mechanism and wherein said clip comprises a second retaining mechanism, said first and second retainer mechanisms coacting to fixedly couple said clip to said housing when said clip is fitted to said back wall.

5. Apparatus of claim 2, wherein said clip comprises a back wall and two side walls, two cams each extending along a corresponding one of said side walls of said clip, each of the cams having a finger positioned below the lip of said sheath when said housing is in said first position, the fingers pushing against the lip of said sheath to remove said sheath from said base when said housing is pivotally move to the direction away from the longitudinal axis of said base.

6. Apparatus of claim 1, wherein said housing comprises a lower portion having a back wall pivotally connected to said base, said back wall having an opening and two adjacent loops that extend from said back wall toward the interior of said housing, said loops each lockingly grasping a corresponding hook formed at a rib that faces said back wall at said base when said housing is pivotally moved toward said base and comes into substantial alignment along the longitudinal axis of said base after said sheath is removed from said base.

7. Apparatus of claim 1, wherein said apparatus comprises a needle assembly having a receptacle end adapted to connect the needle assembly to a syringe.

8. Apparatus of claim 1, wherein said apparatus comprises a needle assembly and wherein once said needle assembly is connected to a syringe, the operation of removing said sheath from said needle assembly is effected with a one handed movement of a user who holds said syringe with one hand and pivotally moving said housing with a digit of his one hand to said second position.

9. Apparatus of claim 1, wherein said apparatus comprises a blood collection tube holder and wherein said base comprises a neck extending from a closed end of said tube, the needle being a double ended needle that mates to said neck, said housing being rotatably mounted to said neck or non-rotatably molded integrally to said neck as a one piece apparatus.

10. Apparatus of claim 1, wherein said apparatus comprises a syringe and wherein said base comprises the needle end of said syringe.

11. Apparatus of claim 1, wherein said base and said housing are mold integrally in one piece from a material having a color that designates the gauge of the needle extending from said base.

12. Needle assembly comprising: a base with a needle end to which a needle extends and a receptacle end adapted to connect the needle assembly to a luer of a syringe, a needle protective housing having a back wall and two side walls each extending from said back wall pivotably connected to said base, a sheath non-fixedly mated to said base to cover the needle extending therefrom prior to use thereof, said sheath having an open end that frictionally contacts said base so as not to be removable from said base without a predetermined force applied thereto longitudinally along the axis of said base toward the needle to remove it from said base, wherein said housing comprises two cams each extending from a corresponding one of the side walls of said housing, each of said cams having a finger positioned below a lip at the open end of said sheath when said housing is at said first position in relative proximity to said sheath when said sheath is mated to said base and covers the needle, the finger of each of said cams pushing against the lip of said sheath with at least the predetermined force against said sheath to remove said sheath from said base when said housing is pivotally moved from said first position toward a second position away from the longitudinal axis of said base.

13. Needle assembly of claim 12, wherein said back wall comprises an aperture and wherein said clip comprises an anchor that snap fits into the aperture to fixedly couple said clip to said housing.

14. Needle assembly comprising: a base with a needle end to which a needle extends and a receptacle end adapted to connect the needle assembly to a luer of a syringe, a needle protective housing having a back wall and two side walls pivotably connected to said base, a sheath non-fixedly mated to said base to cover the needle extending therefrom prior to use thereof, said sheath having an open end that frictionally contacts said base so as not to be removable from said base without a predetermined force applied thereto longitudinally along the axis of said base toward the needle to remove it from said base, wherein said housing being in a first position in relative proximity to said sheath when said sheath is mated to said base and covers the needle, said housing pivotable from said first position toward a second position away from the longitudinal axis of said base, wherein said needle assembly further comprising a clip separate from said housing but configured to conform with at least the lower portion of said housing so that said clip is attachable to at least a portion of said housing, said clip having at least one cam positioned below a lip that form the open end of said sheath when said clip is attached to said housing for removing said sheath from said base when said housing is pivotally moved toward said second position.

15. Device for removing a sheath from a needle assembly having a base to which said sheath is removably mated, the sheath covering a needle extending from said base, said sheath having an open end that frictionally contacts said base so as not to be removable from said base without a predetermined force applied thereto longitudinally along the axis of said base toward the needle, said sheath having a circumferential lip at its open end, the device comprising:

a one piece needle protective housing pivotably connected to said base having two cams each extending from a corresponding side wall of said housing positioned below the lip of said sheath with said housing being in a first position in relative proximity to said sheath when said sheath is mated to said base and covers the needle, each of said cams having a finger that pushes against the lip at the open end of said sheath to remove said sheath from said base when said housing is pivotally moved from said first position toward a second position away from the longitudinal axis of said base.

16. Device for removing a sheath from a needle assembly having a base to which said sheath is removably mated, the sheath covering a needle extending from said base, said sheath having an open end that frictionally contacts said base so as not to be removable from said base without a predetermined force applied thereto longitudinally along the axis of said base toward the needle, said sheath having a circumferential lip at its open end, the device comprising:

a needle protective housing having a back wall and two side walls pivotably connected to said base, said housing being in a first position in relative proximity to said sheath when said sheath is mated to said base and covers the needle;

wherein said device further comprising a clip separate from said housing but configured to conform with at least the lower portion of said housing so that said clip is attachable to said housing, said clip having the at least one cam positioned below the lip of said sheath when said clip is attached to said housing for pushing against the lip of said sheath to remove said sheath from said base when said housing is pivotally moved away from the first position.

17. Device of claim 16, wherein said back wall comprises a first retaining mechanism and wherein said clip comprises a second retaining mechanism, and wherein said first and second retainer mechanisms coact to fixedly couple said clip to said housing when said clip is fitted to said housing.

* * * * *